(12) United States Patent
Pinelli

(10) Patent No.: US 10,154,999 B2
(45) Date of Patent: Dec. 18, 2018

(54) CAFFEINATED GUMMIES

(71) Applicant: Punch'd Energy Incorporated, Livermore, CA (US)

(72) Inventor: John Pinelli, Melbourne, FL (US)

(73) Assignee: Punch'd Energy Incorporated, Melbourne (Viera), FL (US)

( * ) Notice: Subject to any disclaimer, the term of this patent is extended or adjusted under 35 U.S.C. 154(b) by 0 days.

(21) Appl. No.: 15/063,627

(22) Filed: Mar. 8, 2016

(65) Prior Publication Data

US 2017/0258799 A1   Sep. 14, 2017

(51) Int. Cl.

| | | |
|---|---|---|
| *A61K 31/522* | (2006.01) | |
| *A61K 9/00* | (2006.01) | |
| *A61K 47/46* | (2006.01) | |
| *A23G 3/48* | (2006.01) | |
| *A23G 3/42* | (2006.01) | |
| *A23G 3/36* | (2006.01) | |
| *A23L 1/0562* | (2006.01) | |
| *A23L 1/0524* | (2006.01) | |
| *A23L 1/30* | (2006.01) | |

(52) U.S. Cl.
CPC .............. *A61K 31/522* (2013.01); *A23G 3/36* (2013.01); *A23G 3/42* (2013.01); *A23G 3/48* (2013.01); *A23L 1/0524* (2013.01); *A23L 1/05625* (2013.01); *A23L 1/30* (2013.01); *A23L 1/3002* (2013.01); *A61K 9/0056* (2013.01); *A61K 47/46* (2013.01); *A23V 2002/00* (2013.01)

(58) Field of Classification Search
CPC .... A61K 31/522; A61K 47/46; A61K 9/0056; A23G 3/36; A23G 3/42; A23G 3/48; A23L 1/0524; A23L 1/05625; A23L 1/30; A23L 1/3002; A23V 2002/00
See application file for complete search history.

(56) References Cited

U.S. PATENT DOCUMENTS

| | | | |
|---|---|---|---|
| 2008/0063748 A1* | 3/2008 | Massey | A23G 3/0068 426/6 |
| 2009/0142443 A1* | 6/2009 | Robinson | A23G 4/20 426/5 |
| 2014/0308374 A1* | 10/2014 | Goel | A61K 45/06 424/735 |

OTHER PUBLICATIONS

Energy Gummi Bears "Nutrition", web page, <http://energygummibears.com/nutrition>, accessed Jun. 27, 2017.

* cited by examiner

*Primary Examiner* — Sarah Pihonak
(74) *Attorney, Agent, or Firm* — Gardner Groff Greenwald & Villanueva, PC

(57) ABSTRACT

Described herein are gummy compositions and products. In one aspect the gummy compositions include:
(I) one or more gelating agents;
(II) at least one fruit juice and/or fruit extract; and
(III) 0.15-2 wt % caffeine.
In a further aspect the invention provides a gummy composition comprising:
(I) one or more gelating agents;
(II) at least one fruit juice and/or fruit extract;
(III) at least one vitamin; and
(IV) 0.15-2 wt % caffeine.
Also described herein are gummy products composed of the gummy compositions as well as methods of making and using the gummy compositions.

29 Claims, 1 Drawing Sheet

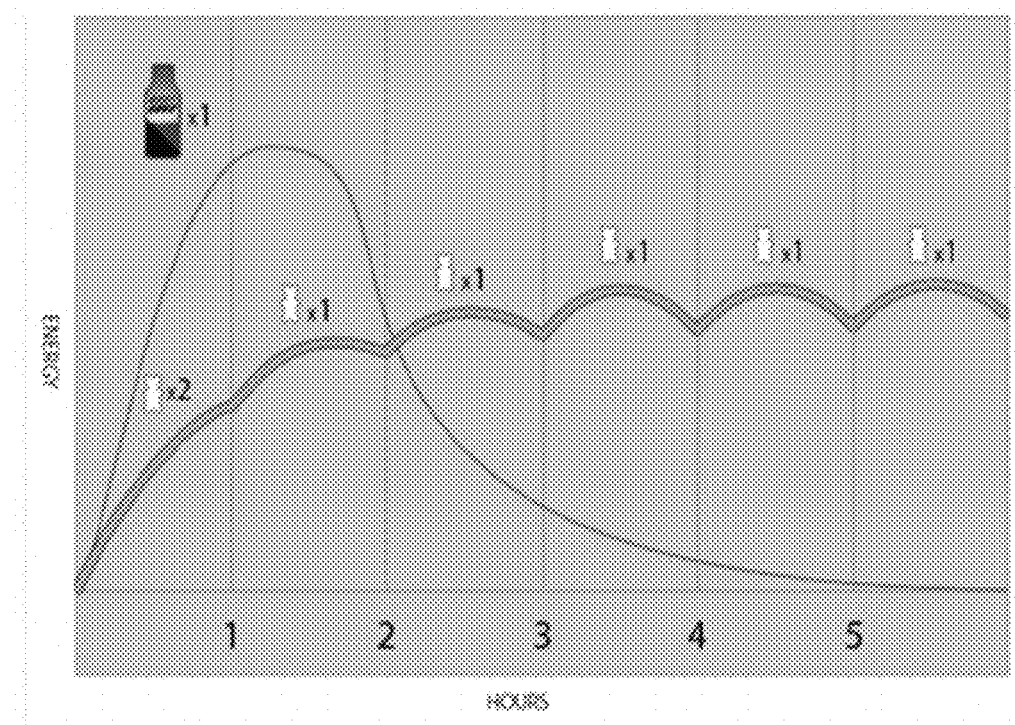

CAFFEINATED GUMMIES

FIELD OF THE INVENTION

The present invention relates to gummy compositions containing caffeine and fruit juice or an extract thereof, gummy pieces made therefrom and uses thereof. In particular, the invention provides an alternative to caffeinated energy drinks and sodas, allowing the consumer to fit their caffeine intake to their individual needs.

BACKGROUND TO THE INVENTION

For many, a significant source of caffeine comes from drinks. These are beverages that provide an individual with an energy surge that lasts for a variable period of time. Coffee, which is perhaps the best known caffeinated drink, derives all of its energy enhancing properties from caffeine.

A distinction needs to be drawn between perceived energy and calorific energy. Tea and coffee, particularly espresso, are classic examples of drinks which themselves have little calorific content, unless combined with milk and/or sugar, yet provide a perceived increase in a consumer's alertness or energy levels. The term "energy drinks" is typically used to describe drinks which increase not only perceived energy levels but also provide calorific content, usually in the form of sugar. A classic example would be Lucozade®. Other examples of "energy drinks" include Red Bull®, Monster®, various colas etc.

Since caffeine itself is bitter, flavours are added to mask its taste. Typically in addition to high levels of caffeine, energy drinks contain high levels of sugar or sweeteners or other bitter taste blocking ingredients such as sodium, sorbitol or taurine. This often leads to energy drinks that are very sugary with a medicinal, sickly and artificial taste.

One disadvantage of providing caffeine in liquid form is that consumers tend to consume their drink to quench thirst rather than simply for the caffeine content. They may therefore take in more caffeine in one serving than they need to keep them alert or is good for them. This leads to the consumer experiencing energy highs and lows. In the case of some energy drinks the surge in caffeine may also be accompanied with a surge in blood sugar levels, which is bad for health, particularly where the consumption of these drinks is a regular occurrence.

Energy drinks are typically sold in a standard size with a particular caffeine content. Consumers commonly perceive that they should consume an entire energy drink in one sitting, meaning that the amount of caffeine consumed per bottle is the same regardless of size, gender, caffeine tolerance of the individual and so on. This can be vastly in excess of what a consumer actually needs to achieve the feeling of being alert or energized.

Caffeine ingested via energy drinks is primarily absorbed through the gastrointestinal tract. Orally ingested caffeine typically takes 30-45 minutes to achieve maximum absorption. When consuming caffeinated drinks there is therefore a lag between the beginning of caffeine intake and the consumer's perception of their energy/alertness levels. As a result, the consumer often takes in more caffeine than they really need or want to consume. There are therefore problems with energy drinks.

Consumers are becoming ever more health conscious and are seeking alternatives to existing caffeinated drinks. In particular, consumers are looking towards natural products which are lower in sugar and provide a caffeine fix without the disadvantages of energy drinks. Coffee and tea are a more healthy alternative but are not a portable solution and are not readily available at all times. Also coffee uses roasted natural caffeine and if the beans are over-roasted then they can become toxic leading to a number of adverse consequences for the drinker.

One alternative produced by Loud Truck® are "energy gummy bears" which are gummy compositions containing caffeine from guarana extract. These "energy gummy bears" are marketed in a packet containing 9 gummies and contain a total caffeine content of 32 mg (3.5 mg/piece). An advantage of providing caffeine in non-liquid form is that as it is chewed the caffeine is absorbed through the lining of the cheeks and the tissues in the mouth more rapidly and efficiently than through the GI tract and thus counters fatigue more rapidly.

The level of caffeine in existing gummy products is still low and a consumer would need to consume over 20 pieces to have the same caffeine intake as a regular coffee from a typical coffee outlet.

It would therefore be advantageous to provide a caffeinated gummy product which would have a higher caffeine content per piece because the product would then be truly portable and not require the consumer to carry around large quantities of gummies which is impractical. Furthermore this would enable consumers to have a longer lasting caffeine hit and would also discourage consumers from consuming too many pieces in one sitting. Given the sugar content per gummy, eating too many gummies is not ideal. That requires an increase in the content of caffeine within each gummy piece. However, as previously noted, any increase in caffeine content leads to organoleptic problems due to the bitterness of caffeine.

Existing caffeine gummies use high levels of sugar and artificial sweeteners to mask the taste of caffeine. Existing caffeine gummies contain artificial sweeteners like sorbitol which is a laxative and whose daily consumption needs to be restricted. There is therefore a need for a low-sugar alternative, laxative free product with a higher caffeine content.

The present inventors have now found that a particular flavouring is capable of masking the taste of caffeine even when caffeine levels within the gummy composition are high, and can simultaneously achieve this without requiring sugar levels as high as in existing gummies

SUMMARY OF THE INVENTION

In a first aspect the invention provides a gummy composition comprising:
(I) one or more gelating agents;
(II) at least one fruit juice and/or fruit extract; and
(III) 0.15-2 wt % caffeine.

In a further aspect the invention provides a gummy composition comprising:
(I) one or more gelating agents;
(II) at least one fruit juice and/or fruit extract;
(III) at least one vitamin; and
(IV) 0.15-2 wt % caffeine.

In a further aspect the invention provides a gummy product comprising or consisting of a gummy composition as herein defined. The gummy product preferably has a weight of 2.5-3.5 g per piece and contains caffeine in an amount of 5-30 mg/piece.

In a further aspect the invention provides a process for the preparation of a gummy composition comprising combining
(I) one or more gelating agents;
(II) at least one fruit juice and/or fruit extract; and
(III) 0.15-2 wt % caffeine; and
(IV) optionally water;
at a temperature above the gelating temperature of the one or more gelating agents so as to form a liquid blend; and allowing said liquid blend to gel to form said gummy composition.

The invention also provides a gummy produced by the process hereinbefore defined.

In a further aspect the invention provides a gummy product as herein described for use in the cosmetic treatment of or prevention of fatigue.

In another aspect the invention provides a method of treatment or prevention of fatigue comprising consuming one or more gummy products according to the invention, e.g. every 30-60 minutes for a total period of 2-8 hours.

In another aspect the invention provides a container having indicia on its external surface and containing gummy products according to the invention.

BRIEF DESCRIPTION OF THE DRAWINGS

The accompanying drawings, which are incorporated in and constitute a part of this specification, illustrate several aspects described below.

FIG. 1 is a pictorial illustration of a consumer's perceived energy levels when consuming gummy pieces according to the invention, against the perceived energy levels when consuming an energy drink.

DETAILED DESCRIPTION OF THE INVENTION

The present invention provides gummy compositions containing caffeine. The term "gummy" as used herein is a term of the art and any gummy composition which provides the necessary texture can be used. Gummy products are chewable and most often classified as candies. The texture of a gummy is in part a result of the presence of a gelating agent such as gelatin, although vegetarian-friendly substitutes as known in the art can be used without impacting on the texture. Particularly preferred gummy compositions of the invention include one or more gelating agents selected from gelatin and/or pectin. The level of gelating agent is not crucial so long as the texture of a gummy is achieved, but typical levels in a composition of gummy piece of the invention are 1 to 50 wt % gelating agent, such as 2 to 25 wt %, especially a level of 4 to 10 wt. %. A level of about 6% is particularly favoured. This relative low gelating content is favoured to ensure the gummies are compressible. Note that in any gummy, the balance of the weight content of the composition is water. This may be added water or may derive from the fruit juice.

Sugars and Calorific Content

Typically, the majority of the calorific content of gummies of the invention will come from fruit juice or fruit extract. These contain some simple sugars as well as more complex polysaccharides. As used herein, "simple sugars" or "sugar" means mono or disaccharides unless otherwise stated. In some embodiments of the invention, the gummies may contain only monosaccharides as sugars (such as fructose). Gummies of the invention will preferably have a sugar content of 20-40 wt. %, preferably 25-40 wt. %, such as 30-36 wt. %.

Existing gummies from Loud Truck have a calorific content of 60 calories per pack of 8 gummies, which corresponds to a ratio of 60 calories (60 kcal) per 32 mg of caffeine, i.e. about 2 kcal/mg of caffeine. As described herein, the invention aims to increase the relative caffeine content whilst keeping the calorific content stable or even reducing the calorific content. It is therefore preferred that gummy compositions of the invention have a calorific content of 1.5 kcal/mg of caffeine or less, preferably 1.2 kcal/mg of caffeine or less, such as 1.0 kcal/mg of caffeine or less, such as 0.8 kcal/mg of caffeine or less. A level of 0.6±0.1 kcal/mg of caffeine is particularly appropriate in some embodiments.

Caffeine Content

Gummy compositions of the invention contain a higher proportion of caffeine than is present in existing caffeine gummies, such as those produced by Loud Truck®. Existing gummies are marketed as 32 mg caffeine per 1 oz (28.34 g) pack of 9 gummies, which corresponds to about 0.11 wt % caffeine, or about 3-4 mg caffeine per gummy piece.

Gummy compositions of the invention contain caffeine at a level of 0.15-2 wt. %, preferably at a level of 0.2-1.6 wt. %, such as 0.2-1.4 wt. % or 0.25-1 wt. %. This corresponds to a preferred caffeine content of 6-60 mg/3 g gummy piece, preferably 7.5-48 mg, such as 7.5-41 mg/3 g piece or 7.5-30 mg/3 g piece. These levels are much higher than the levels of caffeine in existing gummy products. In one preferred embodiment the invention provides a gummy functional fruit snack, also referred to as "gummy product", having a weight of 3±0.3 g per piece and having a caffeine content of 6-36 mg per piece, preferably 7-33 mg, especially 10 to 20 mg per piece.

Caffeine used in gummies of the invention can be obtained from various sources, such as cocoa beans, kola nuts, tea leaves, guarana berries, guayusa, and coffee beans. The present invention preferably uses plant-derived caffeine rather than synthetic caffeine. Ideally, caffeine may come from coffee beans. It is envisaged that plant-derived, or "natural" caffeine has a more appealing taste compared to synthetic caffeine, perhaps as a result of small traces of other natural extracts retained during production of natural caffeine. Caffeine levels or ratios given herein refer to the absolute level of caffeine rather than the sum total of caffeine and other components present in natural caffeine extract. For instance, where a product calls for 0.9 wt. % caffeine and the natural caffeine extract itself is 90 wt % caffeine, the product contains 1.0 wt. % natural caffeine extract.

Additives

In a preferred embodiment therefore, it is a feature of the invention that the gummies of the invention do not contain appreciable levels of asparatame. It is a feature of the invention therefore that the gummies of the invention do not contain appreciable levels of acesulfame potassium. It is a feature of the invention therefore that the gummies of the invention do not contain appreciable levels of corn syrup or corn sugar. It is a feature of the invention therefore that the gummies of the invention do not contain appreciable levels of polyol sweeteners or artificial sweeteners such as sorbitol, maltitol, erythritol, xylitol, isomalt, mannitol, lactitol, hydrogenated starch hydrolysates or the like.

In a preferred embodiment, it is a feature of the invention therefore that the gummies of the invention do not contain appreciable levels of phenylalanine. It is a feature of the invention therefore that the gummies of the invention do not contain appreciable levels of malic acid. It is a feature of the invention therefore that the gummies of the invention do not contain appreciable levels of advantame, neotame or saccharin.

There are a number of studies on the long-term impact of taurine on the brain and also its relationship with caffeine. It is therefore another preferred feature of the invention that gummies of the invention do not contain appreciable levels of taurine.

Unless otherwise stated, a level which is "not appreciable" as used herein is a level of 0.1 wt. % or less of the gummy composition. Preferably the level will be 0.05 wt. % or less, such 0.01 wt. % or less. Preferably, the limits of said component(s) will be below the level of detection, e.g. zero.

Gummies of the invention also preferably contain less than 0.02 wt. % of sodium, preferably less than 0.01 wt. % of sodium, preferably no sodium. A high level of sodium in existing caffeinated products is often indicative of the presence of sugar substitutes, which are commonly sodium derivatives.

Fruit Juices and Fruit Juice Extracts

Caffeine has a bitter taste and existing products contain additives which mask this flavour. The level of caffeine in existing energy gummies is low and/or is masked by flavours and sweeteners such that the consumer does not perceive an unpleasant bitter sensation. It would be expected that on increasing the levels of caffeine to levels as high as the invention the bitter sensation would be significant.

The inventors have now established that it is possible to achieve an organoleptically acceptable gummy product with a higher caffeine content than existing gummy compositions without requiring artificial sweeteners, sugar polyols and other synthetic additives to mask the taste of caffeine. This is achieved by including a fruit juice or fruit juice extract. The inventors are not aware of any caffeinated gummies which have included a fruit juices or fruit juice extracts. Whilst other products may contain artificial fruit flavouring, they do not include actual fruit juice or a fruit juice extract.

Gummy compositions of the invention will comprise one or more fruit juices or fruit juice extracts preferably selected from grapefruit juice, grape juice, orange juice, apple juice, peach juice, lemon juice, tangerine, cherry, pineapple and lime juice. The quantity of these fruit juices should be high enough to sufficiently mask the bitterness of the caffeine. The amounts of fruit juices needed will naturally depend on the level of caffeine contained within the gummy The gummy composition of the invention may comprise 20 to 80 wt. % of fruit juices/extract, such as 25 to 70 wt. % of fruit juices/extract, especially 30 to 75 wt. % fruit juices/extract, most preferably 35 to 70 wt. % fruit juices/extract, especially about 45±5 wt. %. In one embodiment of the invention, all water in the gummy is deemed to be part of the fruit juice extract. Thus, in another embodiment, the combined content of water and fruit juice/fruit juice extract may comprise 20 to 80 wt. % of the composition, such as 25 to 70 wt. % of the composition, especially 30 to 75 wt. % of the composition, most preferably 35 to 70 wt. % of the composition, especially about 45±5 wt. %.

In one embodiment it is possible to use a mixture of different fruit juices. A mixture of citrus and non-citrus fruit juices is especially preferred as that has been found to mask the caffeine bitterness whilst using a low level of the material.

The term fruit juice is used herein in its conventional sense to refer to the juice extracted from a fruit, optionally filtered to remove pulp. The juice in question might therefore be unchanged (e.g. like freshly squeezed juice) or filtered. Alternatively, the fruit juice may be a concentrate, i.e. a fruit juice extract. Concentrated fruit juice may be processed to remove a defined proportion of the natural water content found in the fruit to produce a product that is approximately 3 to 7 times more concentrated and therefore smaller in volume than the natural juice. Juice/extracts of the invention may also be filtered to remove pulp. Juices/extracts may also be pasteurised. Fruit juice extracts according to the invention are fruit juices from which the water content has been reduced or removed.

The inventors have found that it is possible to mask the bitterness of caffeine even at loadings of about 20 mg caffeine/3 g piece, in particular when a citrus juice or citrus juice extract is included. In this embodiment the caffeine content in the gummy composition may be as high as 0.4-1.2 wt. %, preferably 0.5-1.1 wt. %, such as 0.6±0.2 wt. %. The citrus juice or extract is preferably selected from grapefruit juice, lemon juice or lime juice in an amount 20 to 80 wt. % of fruit juices/extract, such as 25 to 70 wt. % of fruit juices/extract, especially 30 to 75 wt. % fruit juices/extract, most preferably 35 to 70 wt. % fruit juices/extract, especially about 45±5 wt. %.

Consumers are becoming ever more label savvy and are wise to the health issues caused by over-consumption of sugar, and are becoming cautious about the consumption of synthetic foodstuffs. It is therefore preferred that gummies of the invention contain less than 0.1 wt. % of each of artificial sweeteners, aspartame, acesulfame potassium, advantame, neotame, saccharin, xylitol, sorbitol, erythritol, maltitol, mannitol, lactitol, isomalt, hydrogenated starch hydrolysate, phenylalanine and malic acid, preferably less than 0.05 wt. % of each component.

In existing energy drinks the total level of sugars is extremely high. The presence of sugar not only masks the bitterness of caffeine but also contributes to the enjoyment of these drinks as it provides a separate "real" energy rush from an increase in blood sugar rather than merely a perceived alertness due to caffeine. As is illustrated in Table 1, the ratio of caffeine:sugar (w/w) in some existing energy drinks is between 1:300 to upwards of 1:1000. Existing gummy compositions from Loud Truck® have a caffeine: total sugars value of about 1:400.

Of course, these high sugar levels are required to try to mask the caffeine bitterness. It is a further aim of the present case to mask the task of caffeine using a fruit juice or extract thereof and hence without a high level of sugar. Where there are lower levels of sugar then the current manufacturers have used artificial sweeteners like sorbitol or sodium-based compounds to mask the bitterness of the caffeine. We do not use these compounds either.

Gummy compositions of the invention have a caffeine to sugar ratio which is much lower than existing caffeinated energy drinks or caffeinated gummies This is achieved without compromising the organoleptic properties of the gummy by a careful use of fruit juices and appropriate caffeine content. It is preferred that in gummy compositions of the invention the ratio of caffeine:total sugars (w/w) is less than 1:200, preferably less than 1:150, particularly preferred levels are 1:100±30. The minimum may be 1:50 caffeine to sugar. The sugar present in the claimed gummies preferably derives from the natural ingredients added, e.g. the fruit juice and potentially from a small amount of added sugar, e.g. from sugar beet/cane, brown rice syrup or organic tapioca. It is preferred that each 3 g gummy piece has fewer than 6 calories, preferably fewer than 4 calories. Stated alternatively, the calorific content of the gummy composition is preferably less than 2.2 kcal/g, preferably less than 2.1 kcal/g, 2.0 kcal/g or less is particularly preferred. The low ratio of caffeine:total sugar is indicative of the fact that our gummies are simultaneously high in caffeine but low in calories.

Vitamins

Gummies of the invention could also be fortified with vitamins or other essential compounds. For example, vitamin C could be added to the gummies Other vitamins of interest include vitamins A, D and E. It may be necessary to add antioxidants etc. (although ascorbic acid acts as an antioxidant). Other components of interest include preservatives such as citric acid, which may be present in significant amounts where citrus fruit juices such as grapefruit, lemon or lime juice are included.

Preparation

The manufacture of the gummy compositions of the invention involves well known processes. The components of the gummy are typically combined at elevated temperature, i.e. above the temperature at which the gelating agent will gel. Often warm water (e.g. 60 to 80'C water) will be used to ensure that the components, in particular the gelating agents, are in liquid form at this point. What is formed is therefore a solution of the components (although some particulates e.g. from the fruit juice may remain).

Once mixed, the gummy composition can be formed into moulds and cooled to allow gelling to occur. The formation of gummy compositions is therefore a well-known process and it does not need further explanation here. It is the same process used at home to make Jell-O: hot water melts the gelating agent(s), blending of ingredients occurs in the molten gelating agent and gelation is encouraged via cooling.

It may be that the fruit juice can act as a source of most of the water needed to prepare the gummy composition. The person skilled in the art can devise suitable manufacturing processes.

Pieces

The gummy compositions of the invention will typically be provided in the form of individual gummy pieces. The pieces are preferably moulded into a shape to increase their consumer appeal, e.g. bears, geometric shapes and company logos, using conventional methods known in the art.

Method

Another aspect of the invention involves a method of treating or preventing fatigue, involving consuming the gummy composition of the invention, or consuming one or more gummy products of the invention. It will be appreciated that consumption of gummies of the invention causes a perceived energy rush and therefore the treatment is preferably non-therapeutic.

In particular, the method preferably involves consuming the gummy pieces at regular intervals so as to maintain a more uniform caffeine level that is not achieved either with energy drinks or with existing caffeinated gummy formulations.

The inventors have found that a particularly effective method involves consuming 1-4 gummy products according to the invention every 30-60 minutes for a total period of 2-8 hours, such as 2-6 hours. The frequency and number of gummies needed with each serving can be self-tailored to the gender, size and caffeine tolerance and activity of the consumer.

One particularly preferred method involves initially consuming 2-4 gummies according to the invention within the first hour (t=0 being defined as the time of consuming the first gummy), and subsequently consuming 1-2 gummies every subsequent hour, for a period of in total 2-8 hours, such as 2-6 hours. As described herein, the number of gummies consumed and frequency will depend on the consumer. However, a particularly suitable method involves consuming 1-2 gummies within the first hour, and subsequently consuming 1 gummy for each subsequent hour for a period of 2-8 hours. This maintains a consumer's perceived energy levels at a more steady level and thereby prevents the consumer experiencing energy highs and lows.

The invention also provides a container, such as a sealed plastic packet, containing 5-30 gummy pieces according to the invention. The container may include on its external surface advertising indicia, such as company logos, nutritional information etc. . . . The indicia may also contain instructions for combating fatigue according to the method of the invention.

The gummies of the invention are able to provide the consumer with a quick and potentially high "hit" of caffeine. The gummies are portable and hence easy to use anywhere and at any time. As the amount of caffeine in each gummy is known to the consumer, the consumer can dose himself with the amount of caffeine the desires simply by eating the correct number of gummies As a chewed product remains in the oral cavity for a prolonged period (as opposed to a drink), the caffeine released during the chewing process can be absorbed through the cheek lining and other tissues of the mouth (buccal mucosa) and hence the gummies of the invention are able to counter fatigue more rapidly than energy drinks. Whereas caffeine from drinking coffee typically only has a noticable effect on a consumer's alertness levels after 10 minutes or more, gummies of the invention can raise a consumer's alertness levels in less than half that time.

Moreover, gummies have an excellent shelf life and do not need refrigeration. Moreover, they are light and easier to ship than an energy drink.

EXAMPLES

Lime Gummies

A lime flavoured gummy was prepared as follows.

Water has heated in a cooking vessel then gelatin and pectin were added with mixing until fully dissolved. Subsequently, natural key lime flavour, clarified lime juice concentrate, white grape juice concentrate, citric acid, ascorbic acid, organic tapioca, brown rice syrup and organic cane sugar were added. Natural caffeine from coffee beans was added to achieve a content of 10 mg of caffeine in each gummy piece. The mixture was poured into molds and allowed to cool in a dry place overnight. The pieces were then tumbled with natural oil and natural wax to produce the finished product.

Each gummy piece was 3 g in weight. The total sugar content of each piece was 33 wt % derived from the fruit juice extracts and the cane sugar added. The gelating agents formed 6 wt % of the material. The total fruit juice concentrate content added was 47 wt %.

Tables 1 and 2 show selected nutritional information for a representative gummy of the invention against the existing caffeine gummies from Loud Truck, with other caffeinated energy drinks.

For a caffeine content of 80 mg, it can be seen that the invention has less than half the calories of the next least calorific product (Red Bull®), and less than 3 times the sugar content of the nearest product (Red Bull® or Monster®). The invention also has negligible sodium content compared to other energy products.

TABLE 1

Selected nutritional information for a typical serving size of various caffeinated products.

|  | Serving Size | Sugar g | Calories kcal | Caffeine mg | Sodium mg | Sorbitol | Taurine Mg | Fruit | Wt Ratios Sugar/ Caffeine | RDA % Sodium | Taurine |
|---|---|---|---|---|---|---|---|---|---|---|---|
| Invention | One pack = 8 × 3 g gummies | 8 | 48 | 80 | 0 | 0 | 0 | YES | 100 | 0.0% | 0.0% |
| Loud Truck ® | One pack = 9 × 3 g gummies | 13 | 60 | 32 | 18 | YES | 36 | NO | 406 | 0.8% | 7.2% |
| Red Bull ® | 8.4 fl oz can | 27 | 110 | 80 | 200 | 0 | 1000 | NO | 338 | 8.3% | 200.0% |
| Monster ® | 16 fl oz can | 54 | 200 | 160 | 360 | 0 | 2000 | NO | 338 | 15.0% | 400.0% |
| Coca Cola ® | 12 fl oz can | 39 | 140 | 35 | 45 | 0 | 0 | NO | 1114 | 1.9% | 0.0% |
| Mountain Dew ® | 20 fl oz can | 76 | 290 | 90 | 105 | 0 | 0 | NO | 844 | 4.4% | 0.0% |
| Pepsi Cola ® | 20 fl oz can | 67 | 260 | 63 | 65 | 0 | 0 | NO | 1063 | 2.7% | 0.0% |

TABLE 2

Selected nutritional information for a 80 mg caffeine serving of caffeine of various caffeinated products.

|  | Serving Size | Sugar g | Calories kcal | Caffeine mg | Sodium mg | Sorbitol | Taurine mg | Fruit | Ratios Sugar/ Caffeine | RDA % Sodium | Taurine |
|---|---|---|---|---|---|---|---|---|---|---|---|
| Invention | 1.00 pack | 8 | 48 | 80 | 0 | 0 | 0 | YES | 100 | 0.0% | 0.0% |
| Loud Truck ® | 2.50 packs | 33 | 150 | 80 | 45 | YES | 90 | NO | 406 | 1.9% | 18.0% |
| Red Bull ® | 1.00 can | 27 | 110 | 80 | 200 | 0 | 1000 | NO | 338 | 8.3% | 200.0% |
| Monster ® | 0.50 can | 27 | 100 | 80 | 180 | 0 | 1000 | NO | 338 | 7.5% | 200.0% |
| Coca Cola ® | 2.29 cans | 89 | 320 | 80 | 103 | 0 | 0 | NO | 1114 | 4.3% | 0.0% |
| Mountain Dew ® | 0.89 cans | 68 | 258 | 80 | 93 | 0 | 0 | NO | 844 | 3.9% | 0.0% |
| Pepsi Cola ® | 1.27 cans | 85 | 330 | 80 | 83 | 0 | 0 | NO | 1063 | 3.4% | 0.0% |

The invention claimed is:

1. A gummy piece comprising:
   (I) 4 to 10 wt. % of one or more gelating agents;
   (II) 20 to 80 wt. % a fruit juice, fruit extract, or a combination thereof; and
   (III) 0.15 - 2 wt. % caffeine;
   wherein the gummy piece has a sugar content of 20 to 40 wt. %, and
   wherein components (I)-(III) are present throughout the entire gummy piece; and wherein when the gummy piece comprises sorbitol, it comprises less than 0.1 wt. % of sorbitol.

2. The gummy piece of claim 1 wherein said caffeine is derived from coffee beans.

3. The gummy piece of claim 1 comprising one or more fruit juices or fruit juice extracts selected from grapefruit juice, grape juice, orange juice, apple juice, lemon juice, peach juice, pineapple juice and lime juice.

4. The gummy piece of claim 1 wherein the ratio of caffeine: total sugar (w/w) is less than 1 : 150.

5. The gummy piece of claim 1 comprising less than 0.1 wt. % of each of aspartame, acesulfame potassium, advantame, neotame, saccharin, xylitol, sorbitol, erythritol, maltitol, mannitol, lactitol, isomalt, hydrogenated starch hydrolysate, phenylalanine, or malic acid.

6. The gummy piece of claim 1 having a taurine content of less than 0.1 wt. %.

7. The gummy piece of claim 1 having a sodium content of 0.02 wt. % or less.

8. The gummy piece of claim 1 further comprising citric acid and/or ascorbic acid.

9. The gummy composition piece of claim 1 wherein the level of caffeine is 0.5 - 1 wt % of the piece.

10. The gummy piece of claim 1 wherein the piece comprises a citrus fruit juice or fruit juice extract.

11. The gummy piece of claim 1 having a ratio of calorific content (kcal)/g of gummy piece of less than 2.2 kcal/g of gummy piece.

12. The gummy piece of claim 1 having a ratio of calorific content (kcal)/caffeine (mg) of less than 1.5 kcal/mg caffeine per gummy piece.

13. The gummy piece of claim 1 having a ratio of calorific content (kcal)/g of sugar of 5 kcal/g of sugar or more per gummy piece.

14. The gummy piece of claim 1 which is free of sorbitol.

15. The gummy piece of claim 1 comprising 30 to 75 wt % fruit juice or fruit juice extract per gummy piece.

16. The gummy piece of claim 1 having a weight of 2.5 - 3.5 g per piece and containing caffeine in an amount of 5 - 30 mg/piece.

17. The gummy piece as claimed in claim 16 containing caffeine in an amount of 7 - 15 mg/piece.

18. A process for the preparation of a gummy piece of claim 1 comprising combining
   (I) 4 to 10 wt. % of one or more gelating agents;
   (II) 20 to 80 wt. % of at least one fruit juice and/or fruit extract; and
   (III) 0.15-2 wt. % caffeine; and
   (IV) optionally water;
   at a temperature above the gelating temperature of the one or more gelating agents so as to form a liquid blend; and
   allowing said liquid blend to gel to form said gummy piece; and wherein when the gummy piece comprises sorbitol, it comprises less than 0.1 wt % of sorbitol.

19. A gummy piece prepared by the process of claim 18.

20. The gummy piece of claim 1 comprising less than 0.05 wt. % of each of aspartame, acesulfame potassium, advantame, neotame, saccharin, xylitol, sorbitol, erythritol, maltitol, mannitol, lactitol, isomalt, hydrogenated starch hydrolysate, phenylalanine, or malic acid.

21. The gummy piece of claim 1 having a taurine content of less than 0.05 wt. %.

22. The gummy piece of claim 1 not containing any taurine.

23. The gummy piece as claimed in claim 7 having a sodium content of 0.01wt. % or less.

24. The gummy piece of claim 1 not containing any sodium.

25. The gummy piece of claim 1 wherein the gummy product comprises grapefruit juice, lemon juice and/or lime juice.

26. The gummy piece of claim 1 having a sugar content of 25-40 wt. %.

27. The gummy piece of claim 1 having a sugar content of 30-36 wt. %.

28. The gummy piece of claim 1 wherein the gelating agent is gelatin, pectin, or a combination thereof.

29. A method of treatment or prevention of fatigue comprising consuming one or more gummy pieces of claim 1 and subsequently consuming one gummy piece every 30-60 minutes for a total period of 2-8 hours.

* * * * *